United States Patent [19]
Acorn

[11] Patent Number: 5,705,735
[45] Date of Patent: Jan. 6, 1998

[54] BREATH BY BREATH NUTRITIONAL REQUIREMENTS ANALYZING SYSTEM

[75] Inventor: Russell G. Acorn, White Bear Lake, Minn.

[73] Assignee: Medical Graphics Corporation, St. Paul, Minn.

[21] Appl. No.: 695,309

[22] Filed: Aug. 9, 1996

[51] Int. Cl.⁶ .......................... B01D 59/44; F61B 05/08; A61B 05/08; A23L 01/303
[52] U.S. Cl. .................. 073/23.3; 128/718; 128/204.23; 128/671; 204/424; 364/413.03; 422/84; 436/68
[58] Field of Search ..................... 73/23.3, 23.34; 128/716–719, 730, 725, 671, 204.22, 204.23, 204.21, 204.18; 204/424; 364/413.03, 413.02, 413.07; 422/84; 436/68

[56] References Cited

U.S. PATENT DOCUMENTS

| | | | |
|---|---|---|---|
| 4,463,764 | 8/1984 | Anderson et al. | 128/719 |
| 4,572,208 | 2/1986 | Cutler et al. | 128/718 |
| 4,917,108 | 4/1990 | Mault | 128/718 |
| 4,966,141 | 10/1990 | Bacaner et al. | 128/207.14 |
| 4,986,268 | 1/1991 | Tehrani | 128/204.22 |
| 5,042,501 | 8/1991 | Kenny et al. | 128/719 |
| 5,043,576 | 8/1991 | Broadhurst et al. | 250/293 |
| 5,072,737 | 12/1991 | Goulding | 128/718 |
| 5,174,959 | 12/1992 | Kundu et al. | 422/59 |
| 5,178,155 | 1/1993 | Mault | 128/718 |
| 5,179,958 | 1/1993 | Mault | 128/718 |
| 5,223,285 | 6/1993 | DeMichele et al. | 426/72 |
| 5,260,336 | 11/1993 | Forse et al. | 514/560 |
| 5,325,861 | 7/1994 | Goulding | 128/719 |
| 5,398,695 | 3/1995 | Anderson et al. | 128/719 |
| 5,433,193 | 7/1995 | Sanders et al. | 128/204.18 |
| 5,438,980 | 8/1995 | Phillips | 128/204.23 |

OTHER PUBLICATIONS

Open Forum p. 1274 from Respiratory Care Nov. 1991 vol. 36 #11.
The Act of Insight —1995 Nellcor, Puritan, Bennett.
Article from Respiratory Care/Puritan Bennett: Metabolic Monitor —7250.
Biomedical Technology Article entitled, "Metabolic Monitor Combines Mixing Chamber & Breath by Breath Measurement"; vol. 22, No. 1: Jan. 1, 1995.

*Primary Examiner*—Herzon E. Williams
*Assistant Examiner*—J. David Wiggins
*Attorney, Agent, or Firm*—Haugen and Nikolai, P.A.

[57] ABSTRACT

A system for real time, breath by breath sampling of a patient receiving up to 100 percent oxygen to determine nutritional requirements of the patient through indirect calorimetry includes a pneumotach member for measuring the volume rate of flow of inspired and expired gas flow at the patient/endotracheal tube/ventilator connection. A sample line extends from the pneumotach to a gas analyzer which measures the percent concentration of constituent respiratory gases in the expired gas flow. A flowmeter is coupled to the gas analyzer for determining the volume flow rate of the expiratory gas flow through the sample line. A microprocessor control samples the analog electrical signals from the gas analyzer, the flow meter and the pneumotach in a predetermined sequence, dynamically compensating for variations in gas flow rate. The analog electrical signals are converted into digital quantities representative of the analog electrical signals from which the necessary calculations are made to determine nutritional requirements.

7 Claims, 1 Drawing Sheet

BREATH BY BREATH NUTRITIONAL REQUIREMENTS ANALYZING SYSTEM

BACKGROUND OF THE INVENTION

I. Field of the Invention

The present invention relates to an electronic medical instrumentation system, and, more specifically, it pertains to real time breath-by-breath analysis for measuring the respiratory gases of a patient to assess the nutritional requirements of the patient through indirect calorimetry.

II. Description of the Prior Art

Indirect calorimetry is the actual measurement of the cumulative effects of metabolism and considers the net exchange of calories during whole body oxygen consumption and carbon dioxide production. This measurement is an accurate determination of the patient's metabolic rate, including the effects of disease, trauma, eating disorders or treatment at the time of the measurement. Indirect calorimetry testing measures gas exchange at rest and the resting energy expenditure (REE) is obtained. Indirect calorimetry assesses not only the total calories associated with the quantities of oxygen consumed and carbon dioxide produced, but also the substrates metabolized producing the ratio of carbon dioxide produced to oxygen consumed. This ratio is the respiratory quotient (RQ). Feeding and TPN (total parental nutrition) mixtures can be optimized if the REE and RQ values are known thereby improving patient recovery times and outcomes.

Various formulas have been used in clinical settings to predict the nutritional requirements of the patient. However, the conventional use of such formulas does not accurately predict the caloric requirements of most patients. A breath-by-breath analysis is beneficial because changes in metabolism can be detected on a real time basis. The monitoring of the breath-by breath testing data allows the technician to identify any data changes due to the patient's activity. By removing the data associated with movement, a true REE is obtained.

Knowing nutritional requirements is important for patients in a critical care unit to assist in management and weaning of mechanically ventilated COPD (chronic obstructive pulmonary disease) patients, to assess metabolic needs in patients with acute thermal injury and trauma patients, to optimize feeding in chronically ill patients with cancer or lung disease, to determine optimal feeding and outcome of critical care patients with sepsis or ARDS (adult respiratory distress syndrome), to diagnose accurately and manage patients with metabolic and/or eating disorders, to assist patients undergoing cardiac rehabilitation, and to assist weight loss patients and individuals in athletic training. Serious consequences can result from over and under feeding patients, especially those in a critical care environment. The length of hospital stays and ventilator days are reduced to affect patient outcomes positively while reducing costs when critical care patients are managed utilizing indirect calorimetry.

The difficulties associated with estimating caloric requirements by formulas are obviated by the direct measurement of oxygen consumption and $CO_2$ production associated with the sum of resting metabolism, thermogenesis, physical activity, and the caloric effects of the disease or treatment. A period of metabolic stability must be identified for a specific gas exchange measured at the mouth to represent cellular gas exchange and provide a ratio that is useful in the interpretation of substrate utilization. In most circumstances, five minutes is the minimum "steady state" during which the $VO_2$ should not vary by more than 10 percent (±5% of mean) and the RQ should be stable within 5 percent (±2.5% of mean).

Collection methods for determining respiratory gas exchange must meet several important criteria. The apparatus should ensure comfortable attachment to the patient, prevention of leaks to avoid volume loss or contamination of gas samples, small dead space to reduce mixing of sampled gases, normal inspired and expired resistance, correctly measured inspired oxygen concentration and ease of patient management. Stable, interpretable measurements should be obtainable within a 15 to a 20-minute test. If a patient has not become accustomed to the measurement environment within 15 minutes, the patient is very unlikely to become more settled beyond this time.

Measurements on patients supported by mechanical ventilation require particular attention to technique. The fraction of inspired oxygen ($FIO_2$) selected and delivered to the ventilator blender is usually neither consistent within nor between breaths and is not measured precisely on the ventilator display. While the mixing of air and oxygen in the internal blenders of most standard commercial ventilators is sufficient for standard ventilator support purposes, they may require special attention for gas exchange measurements because a stable $FIO_2$ is a critical factor for measurement. The pressurized gas delivery ventilators increase the chance of leaks throughout the ventilator circuit and around the patient connection at the E-T tube, tracheostomy or cannula cuff. Additionally, new ventilators have a variety of modes, such as the continuous flow-by mode when the patient is actively breathing, which can affect gas exchange measurements as explained below.

Current methods for determining the RQ and nutritional requirements of a patient supported by mechanical ventilation involve measuring the respiratory gas flow at a distance from the patient/ventilator connection. The inspiratory gases are either measured at the ventilator humidifier, in the line extending from the ventilator to the patient or calculated with the Haldane transformation equation based on the expired respiratory gases. However, the inspired respirations are not always consistent with what is measured at the ventilator humidifier or calculated and with what the patient actually receives.

Furthermore, when the patient is on the continuous flow mode, the ventilator must be set to a mode that best matches the patient's breathing rate and then the assessment is taken with the ventilator in the best matching mode. The expiratory gases are measured in the line extending from the patient to the exit port of the ventilator. A pneumotach is inserted into the expired respiratory gasoline of the ventilator assembly or at the ventilator's exhalation port for direct measurement of the expired gases. While the patient-ventilator circuit is left intact, the sampling is not as direct as possible because it is removed from the patient and it uses a ventilator mode that is not identical to the patient's actual breathing.

Difficulties in assessment also exist with spontaneously breathing patients who may or may not be intubated. Such patients may have weakened capacity and a conventional bidirectional pneumotach may not effectively measure the flow rate. Furthermore, the sampling of the respiratory gas can be affected if the pneumotach has excessive dead space.

Measurement of the respiratory gases at the patient/endotracheal tube/ventilator connection has been previously avoided because of the difficulties associated with the timewise aligning of the respiratory measurements with the respiratory gas flow rate. Determining the phase delay between the gas sampling and the breath sampling is extremely critical. The phase delay results from both the transit time of the respiratory gas from the patient to the analyzer and the response time of the analyzer sending its signal to the microprocessor. Improper alignment will affect the calculations for determining the RQ, leading to an improper determination of caloric needs. There is also concern that current pneumotachs and sample line water traps have excessive dead space that will lead to mixing of the respiratory gashes and poor result.

Another barrier to indirect calorimetry is a high fraction of inspired oxygen ($FIO_2$) requirement. The physical laws of gas exchange measurement, in particular the Haldane transformation equation, reduce the accuracy of these calculations as the $FIO_2$ rises above 0.60. In current indirect calorimetry, the application is limited to use when the fraction of inspired air is 0.60 or less. A direct breath-by-breath sampling using the alveolar equation, (oxygen inspired minus oxygen expired), can be used to evaluate an individual receiving an inspired fraction of oxygen greater than 0.60. Another advantage of using the alveolar equation is that the dead space of the pneumotach and the valve attachment between the sample, line and pneumotach do not have to be taken into account during the evaluation. However, use of the alveolar equation has been limited to research because it requires a fast responding analyzer that also properly aligns the data. Because of these limits, its use has been impractical in clinical situations.

Therefore, what is needed is a real time analyzer that measures by breath-by-breath sampling both inspired and expired respiratory gases directly at the patient/endotracheal tube/ventilator connection, dynamically aligns the flow rate data and the gas analyzer data and operates at high $FIO_2$ rates.

SUMMARY OF THE INVENTION

The present invention is a system for analyzing the patient on a breath by breath-basis for use in determining the resting energy expenditure and respiratory quotient of the patient, especially for a patient on mechanical ventilation, CPAP (continuous positive airway pressure) or other respiratory therapy.

In accordance with the preferred embodiment, a bidirectional pneumotach, sufficiently sized for low dynamic flow conditions is coupled to the ventilator circuit at the patient/endotracheal tube/ventilator connection. The pneumotach is coupled to a pressure transducer that sends a signal to a microproceasor for determining the pressure differential as the respiratory gases flow through the pneumotach. The volume rate of flow of the inspired and expired respiratory gases are measured using the pneumotach and differential pressure sensor combination.

A sample line leads from the pneumotach to a respiratory gas analyzer where that gas analyzer is adapted to measure the percentage concentration of a particular gas present in a sample line. A means, such as a vacuum pump, is provided in the sample line for drawing a sample of the respiratory gas through the sample line. An On-airway analyzer means can also be used. Additionally, a flow meter measures the rate of flow of respiratory gases through the sensor.

The microprocessor has means for compensating for the transit time delays between the time that a gas sample is drawn to the sample line and the time the various gas analyzers take to produce their output response. The microprocessor is programmed with known transit time delays at an initial calibration. The variable transit time, a factor dependent on the flow rate of the sample, is computed during the test sampling to insure proper phase delay. The phase delay is then used to time wise align the measured percentage concentration of the particular gas with the measured volume rate of flow of the inspired or expired respiratory gases measured using the pneumotach differential pressure sensor combination.

The sampling may occur, for example, 100 times per second to provide for a relatively continuous update of information being processed by the microprocessor. The microprocessor is programmed to count for each breath and to detect inconsistent breathing patterns, such as those that may be the result of coughing, swallowing, etc.

The system is dedicated to receive the inputs for a real time breath by breath analysis. The system samples and converts the analog signals to digital signals. The microprocessor is programmed to determine the requisite parameters such as the energy expenditure, oxygen consumption, carbon dioxide production, respiratory quotient and other parameters for conducting a nutritional assessment of the patient.

The primary object of the present invention is to provide a system for assessing nutritional needs of a ventilated patient by a breath by breath analysis over a period of metabolic stability that samples the inspired and expired air with a pneumotach located at the patient/endotracheal tube/ventilator connection.

Another object of the present invention is to provide a system for accurately assessing nutritional needs of a ventilated patient with a fraction of inspired oxygen greater than 0.60 through a breath-by-breath analysis over a period of metabolic stability that samples inspired and expired air at the patient/endotracheal tube/ventilator connection.

A further object of the present invention is to provide a system for accurately assessing a patient's nutritional needs by directly measuring breath-by-breath real alveolar gas exchange by dynamically aligning measured respiratory flow and precisely determining the phase delay between the time the sample is introduced into the sample line and the time at which the respiratory gas analyzers generate their outputs indicative of the percentage concentration of the particular gas.

Still another object of the present invention is to use a disposable pneumotach configured to measure flow at a low dynamic range and that can be used in the ventilator circuit at the patient/endotracheal tube/ventilator connection or conventionally in the patient's mouth.

IN THE DRAWINGS

The foregoing features, objects, advantages of the present invention will become apparent from the following detailed description of the preferred embodiment, especially when considered in conjunction with the accompanying drawings in which:

FIG. 1 is a schematic block diagram of the cardiopulmonary performing analyzer incorporating the present invention; and FIG. 2 is a cross sectional view of the pneumotach of the present invention.

DESCRIPTION OF THE PREFERRED EMBODIMENT

Figure 1:
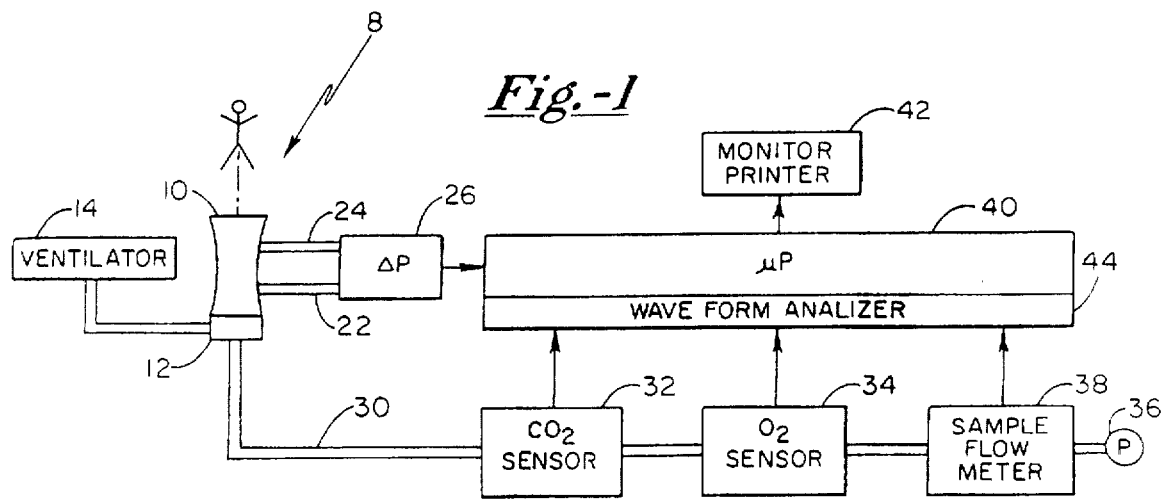

Referring first to FIG. 1, there is shown generally by numeral 8 a pneumotach member that is either placed in the patient's mouth or coupled to the patient/endotracheal tube/ventilator connection 12 of the ventilator 14. A sample line 30 extends from the pneumotach 8 to a $CO_2$ gas analyzer 32 and an $O_2$ gas analyzer 34. A flow meter 38 and pump 36 are adjacent the two gas analyzers. A pressure transducer 26 is also coupled to the pneumotach 8. The gas analyzers 32 and 34, the flow meter and the pressure transducer 26 are linked to a microprocessor 40 and form an analog signaling generating means for producing analog signals representing various characteristics of the gas flow as will be described further below. The microprocessor in turn is linked to a printer and/or monitor 42.

Figure 2:
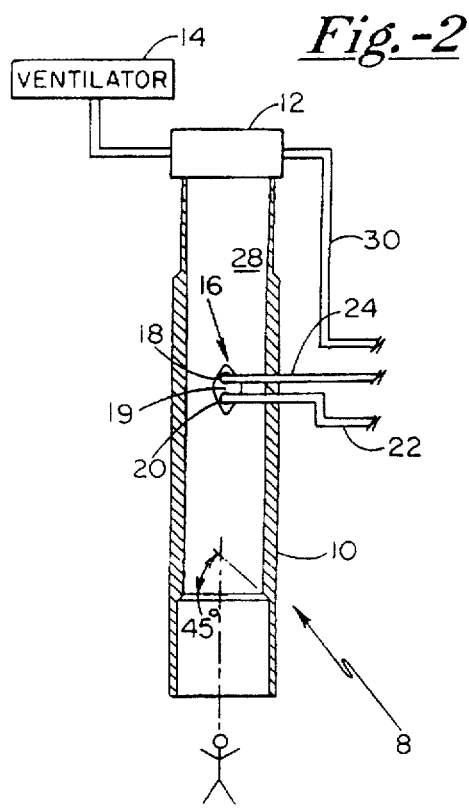

Turning now to FIG. 2, the pneumotach 8 is used to measure the volume rate of both inspiratory and expiratory gases. The pneumotach member 8 consists of a generally tubular open ended barrel member 10 that is preferably molded or otherwise formed from a suitable medical grade plastic or metal such as stainless steel. Plastic is preferred if the mouthpiece is to be a one-time disposable pneumotach. The wall thickness of the tubular member tapers slightly from a minimum at its opposed ends to maximum proximate the midpoint.

A strut 16 is disposed relative to the midpoint of the tubular barrel. The strut has a pair of lumens 18 and 20 separated from one another by a wall 19. A pair of apertures (not shown) passes through the side wall of the tube and separately into the two lumens 18 and 20 of strut 16. The strut 16 preferably has a rhombic cross-sectional configuration and formed along the opposed vertices facing the ends are series of fine apertures (not shown). The plurality of apertures functions as Pitot tubes for two probes 22 and 24. The probes 22 and 24 are coupled to pressure transducer 26 for measuring the pressure differential in the pair of lumens 18 and 20 as respiratory gases pass the exterior of the strut 16.

The pneumotach 8 of this invention operates in the manner taught by Norlien, et al. U.S. Pat. No. 5,038,773 which is incorporated by reference herein. However, the present pneumotach is sized for use at a ventilator patient connection and the pneumotach uses one strut instead of two. The passageway 28 of the barrel 10 is configured as a venturi to increase the flow velocity and insure uniform flow of the respiratory gases over Pitot tube structure. It has an inner diameter of preferably 0.6091 inches. This enables the pneumotach to have a low dynamic range and to be easily coupled to a conventional patient/ventilator connection.

As seen in FIG. 1, sample line 30 extends from the pneumotach 8 to the gas analyzers where a $CO_2$ analyzer 32 and an $O_2$ analyzer 34 assess the percentage concentration of the constituent respiratory gases in the expired gas mixture. The analyzers may be one of a number of commercially available devices. The respiratory gas sample is drawn through the sample line 30 via a pump 36 on the other side of the gas analyzers 32 and 34 for measuring the constituent respiratory gases. Additionally, a flowmeter 38, such as a hot wire type or a mircobridge sensor, is on the sample line 30 just past the analyzers 32 and 34. The outputs from the $CO_2$ and $O_2$ analyzers 32 and 34 are electrical analog waveforms corresponding to the real time $O_2$ or $CO_2$ concentration during the monitored respiratory cycles. The outputs are sent to a waveform analyzer such as that disclosed in U.S. Pat. No. 4,463,764 to Anderson et al and is assigned to Medical Graphics. The contents of that patent are incorporated by reference herein. The waveform analyzer 44 is part of a microprocessor-based system 40 for analyzing analog waveforms.

The waveform analyzer 44 is programmed to compare received waveforms with a predetermined standard, such that waves not conforming to the standard will be eliminated from further processing operations. In this regard, the waveform analyzer 44 may be capable of measuring and storing values corresponding to the peaks of a received waveform and the frequency of incoming signals. The microprocessor 40 also receives analog electrical data from the pressure transducer 26 that produces a voltage output proportional to the differences at the ports, on the pneumotach 8. Furthermore, the flowmeter 38 sends an analog electrical signal proportional to the volume flow rate of the expired gas to the microprocessor. The microprocessor is also programmed to determine the REE, which may be determined by one following the Weir equation:

$$REE=4.18(CHO\ grams/day)+9.46(fat\ grams/day)+(4.32)(protein\ grams/day)$$

where $$CHO\ grams/day=4.12(VCO_2 liters/day)-2.91(VO_2 liters/day)-2.56UN;$$

$$Fat\ grams/day=1.69(VO_2 liters/day)-1.69(VCO_2 liters/day)-1.94UN;$$

$$Protein\ grams\ per\ day=6.25UN$$

$VO_2$ is the oxygen consumption, $VCO_2$ is the carbon dioxide production, CHO is carbohydrates, and UN is the total urinary nitrogen (24 hour urinary nitrogen).

Microprocessor 40 incorporates a dynamic calibration feature as shown in U.S. Pat. No. 5,398,695 to Anderson, assigned to Medical Graphics and which is incorporated by reference herein. The dynamic calibration feature insures that an accurate measurement is obtained by properly accounting for the phase delay. A phase delay results from the time the expired gases travel to the gas analyzers 32 and 34 plus the time that takes for the waveform analyzer 44 to receive the signals from the gas analyzers 32 and 34. Essentially, the calibration feature aligns the phase of the output from the analyzers 32 and 34 with the corresponding flow measurements from the flow meter 38. The microprocessor is programmed to calculate the gas transit time, $t_p$, in the sample line to each of the gas analyzers in accordance with the formula:

$$t_p = t_c(F_c/F_s)$$

With $t_c$ being the gas transit time at a known flow rate, $F_c$ being the known flow rate at calibration and $F_s$ being the flow rate of the gas being sampled. The gas transit time is then added to the known fixed response time of the gas sensor to obtain the phase delay between the expiratory gas flow and the gas concentration measurements.

In operation, if the patient is intubated or ventilated, the pneumotach member 8 is placed at the patient/endotracheal tube/ventilator connection 12. If the patient is not intubated, the pneumotach is placed in their mouth. The reduced diameter of the pneumotach 8 is important for patients in the ICU (Intensive Care Unit) environment whose capacity may be limited or weakened and for connecting to the patient/endotracheal tube/ventilator circuit. If the patient is ventilated, the ventilator may be set to any of its modes, including the flow through mode in which the patient may be actively breathing.

The operation of the device is similar to that in U.S. Pat. No. 4,463,764 patent. Before operation, the desired parameters as set forth in the No. '764 patent, including the measured transit time of a sample through the sample line at a known flow rate are determined at a calibration and entered in the microprocessor. The fraction of inspired oxygen is also entered in the microprocessor 40 and stored so that the appropriate calculations may be carried out. The transit time will be used to determine the phase delay as in U.S. Pat. No. 5,398,695.

The microprocessor is programmed to preferably sample the breath by using approximately 100 samples per second. The microprocessor 40 is programmed to use the alveolar equation (oxygen inspired minus oxygen expired) thus allowing assessment of patients receiving a $FIO_2$ greater than 0.60. The microprocessor accesses, computes and stores the desired parameters for each breath and uses the necessary data to obtain interpretable measurements a percentage of fats, carbohydrates and proteins metabolized daily and the total carbohydrate, fat and protein intake on a per day basis within a 15-20 minute test. The microprocessor then sends data in the desired format to a printer or monitor 42, such as the respiratory quotient, the resting energy expenditure, the flow rate, the percent inspired and expired concentration and output of $CO_2$ and the percent inspired and expired concentration and input of $O_2$. The printed data can also include the following information:

Respiratory rate
Fractional end-tidal $O_2$
Fractional end-tidal $CO_2$
Volume of $CO_2$ per breath
Volume of $O_2$ per breath
Volume of $CO_2$ with dead space
Volume of $CO_2$ per minute
Volume of $O_2$ uptake per minute
Volume of $O_2$ per kilogram
Respiratory exchange rate
Ventilatory equivalent $O_2$
Ventilatory equivalent $CO_2$
$O_2$ pulse
Predicted metabolic rate
Volume $O_2$ per day
Volume $CO_2$ per day
Carbohydrates per day
Fat per day
Protein per day
Total carbohydrates, fat and protein per day
Fat metabolized
Protein metabolized
Percent carbohydrate metabolized
Percent fat metabolized
Percent protein metabolized
Non-protein respiratory quotient
Estimated partial pressure arterial $CO_2$
Partial pressure venous $CO_2$
Partial pressure aveolar $O_2$
Partial pressure aveolar $CO_2$
Alveolar $CO_2$ difference
Breathing reserve
Total volume
Minute ventilation
Metabolic rate per hour
Metabolic rate per minute
Caloric equivalent for $CO_2$
Current burn REE
Body mass index
Protein equipment
REE percent predicted, and/or
Basal metabolic rate percent predicted.

The nutritional needs of the patient can then be determined from the obtained information.

This invention has been described herein in considerable detail in order to comply with the patent statutes and to provide those skilled in the art with the information needed to apply the novel principles and to construct and use such specialized components as are required. However, it is to be understood that the invention can be carried by specifically different equipment and devices, and that various modifications, both as to the equipment details, and operating procedures, can be accomplished without departing from the scope of the invention itself.

What is claimed is:

1. A breath by breath analyzer system for assessing nutritional requirements of an intubated patient, said system comprising:

(a) a pneumotach member coupled to a patient/ endotracheal tube connection, said pneumotach member including means for generating first analog electrical signals proportional to inspired and expired gas flow of said patient, said pneumotach member comprising:
(i) a generally circular passageway having a tapered cross section:
(ii) a strut extending transverse to the longitudinal dimension of said pneumotach member;
(iii) a pair of lumens in said strut;
(iv) a plurality of symmetrically located apertures passing through walls of said strut into said pair of lumens; and
(v) a further pair of apertures passing through a wall of said pneumotach member and individually aligned coaxially with said pair of lumens the passage of inspired and expired gases through said pneumotach member and over said strut creating pressure differential in said pair of lumens;

(b) gas analyzing means coupled to said pneumotach member for producing second analog electrical signals proportional to a percent concentration of constituent gases in said expired gas flow;

(c) flow meter means coupled to said gas analyzing means for producing third analog electrical signals proportional to flow rate of said expired gas flow through said gas analyzing means; and (d) microprocessor means for performing operations in accordance with a stored program of arithmetic instructions for calculating respiratory activity of said patient receiving up to 100% oxygen in inspired gas, said microprocessor including:
(i) waveform analyzer means connected to said gas analyzing means, said pneumotach member and said flowmeter means for sampling said first, second and third analog electrical signals in a predetermined sequence and converting said first, second and third analog electrical signals into digital quantities representative of said first, second and third analog electrical signals during a sampling interval of each and storage means for storing said digital quantities as operands for such arithmetic operations; and
(ii) means for dynamically compensating for variations in the flow rate of said inspired and expired gas flow.

2. The system of claim 1 and further including a pair of hollow needle probes insertable into said pair of apertures in said pneumotach member.

3. The system of claim 1 wherein said passageway has a diameter between 0.5 inch and 0.609 inch.

4. In a breath by breath analyzer system for assessing the nutritional requirement of an intubated patient receiving a fraction of inspired oxygen up to 100%, said system comprising:

(a) a pneumotach member coupled to a patient/endotracheal tube/ventilator connection, said pneumotach member including:
  (i) a generally circular passageway having a tapered cross section;
  (ii) a strut extending transverse to the longitudinal dimension of said pneumotach member;
  (iii) a pair of lumens in said strut;
  (iv) a plurality of symmetrically located apertures passing through walls of said strut into said pair of lumens;
  (v) a further pair of apertures passing through a wall of said pneumotach member and individually aligned coaxially with said pair of lumens, with passage of inspired and expired gases through said pneumotach member and over said strut creating pressure differential in said pair of lumens;
  (vi) coupling means for coupling said pneumotach member to a means for measuring the inspired and expired gas flow; and
  (vii) means for generating first analog electrical signals proportional to inspired and expired gas flow of said patient;

(b) gas analyzing means coupled to said pneumotach member for producing second analog electrical signals proportional to a percent concentration of constituent gases in said expired gas flow of said patient;

(c) flowmeter means coupled to said gas analyzing means for producing third analog electrical signals proportional to a flow rate of said expired gas flow through said gas analyzing means;

(d) microprocessor means for performing operations in accordance with a stored program of arithmetic instructions, said microprocessor including:
  (i) waveform analyzer means linked to said gas analyzing means, said pneumotach member and said flowmeter means for sampling said first, second and third analog electrical signals in a predetermined sequence and converting said first, second and third analog electrical signals into digital quantities representative of said first, second and third analog electrical signals during a sampling interval of each and storage means for storing said digital quantities as operands for such arithmetic operations; and
  (ii) means for dynamically compensating for transit time delays between a time a gas sample is drawn into a sample line and a time said gas analyzing means produce a predetermined output response and for time-wise aligning said measured percentage of concentration of a particular constituent gas with said measured flow rate of inspired and expired gases.

5. The system of claim 4 and further including a pair of hollow needle probes insertable into said pair of apertures in said pneumotach member.

6. The system of claim 4 wherein said passageway has a diameter between 0.5 inch and 0.609 inch.

7. The system of claim 4 wherein said pneumotach member is coupled to a differential pressure transducer.

* * * * *